(12) United States Patent
Levin

(10) Patent No.: US 9,668,824 B2
(45) Date of Patent: Jun. 6, 2017

(54) CUSTOMIZED ROOT CANAL OBTURATION CORES AND METHODS OF MAKING CUSTOMIZED ROOT CANAL OBTURATION CORES

(71) Applicant: Martin David Levin, Bethesda, MD (US)

(72) Inventor: Martin David Levin, Bethesda, MD (US)

( * ) Notice: Subject to any disclaimer, the term of this patent is extended or adjusted under 35 U.S.C. 154(b) by 177 days.

(21) Appl. No.: 14/460,970

(22) Filed: Aug. 15, 2014

(65) Prior Publication Data

US 2016/0045282 A1    Feb. 18, 2016

(51) Int. Cl.
*A61C 5/04*        (2006.01)
*A61C 9/00*        (2006.01)
(Continued)

(52) U.S. Cl.
CPC ............... *A61C 5/04* (2013.01); *A61B 5/055* (2013.01); *A61B 6/14* (2013.01); *A61C 5/50* (2017.02);
(Continued)

(58) Field of Classification Search
CPC ... A61C 5/04; A61C 13/0019; A61C 13/0004; A61C 9/0053; A61C 13/0013; A61C 13/0018; B29C 67/0088; G05B 19/4097; A61B 5/055; A61B 6/14; B33Y 50/02; B33Y 10/00; B33Y 80/00
See application file for complete search history.

(56) References Cited

U.S. PATENT DOCUMENTS

| 6,264,471 B1 | 7/2001 | Martin |
| 2010/0092923 A1 | 4/2010 | Stites |

(Continued)

FOREIGN PATENT DOCUMENTS

| CN | 101803958 A | 8/2010 |
| CN | 103083094 A | 5/2013 |

(Continued)

OTHER PUBLICATIONS

International Search Report and Written Opinion for International Appl. No. PCT/US2015/044842, European Patent Office, mailed on Oct. 16, 2015, 14 pages.

(Continued)

*Primary Examiner* — Rex R Holmes
(74) *Attorney, Agent, or Firm* — Sterne, Kessler, Goldstein & Fox P.L.L.C.

(57) ABSTRACT

A core for obturating a root canal includes a body that has a pre-formed contour that closely matches a contour of the root canal. When the core is inserted in the root canal with or without sealer, there are essentially no voids in the root canal. A method of making a customized root canal obturation core includes generating a three-dimensional image of a root canal. The method also includes manufacturing the customized root canal obturation core based on the three-dimensional image of the root canal. The customized root canal obturation core has a preformed contour that closely matches a contour of the root canal such that when the core is inserted in the root canal with or without sealer there are essentially no voids in the root canal.

28 Claims, 14 Drawing Sheets

(51) Int. Cl.

| | | |
|---|---|---|
| *A61C 13/00* | (2006.01) | |
| *A61B 6/14* | (2006.01) | |
| *A61B 5/055* | (2006.01) | |
| *G05B 19/4097* | (2006.01) | |
| *B29C 67/00* | (2017.01) | |
| *A61C 5/50* | (2017.01) | |
| *B33Y 80/00* | (2015.01) | |
| *B33Y 10/00* | (2015.01) | |
| *B33Y 50/02* | (2015.01) | |

(52) U.S. Cl.
CPC ........ *A61C 9/0053* (2013.01); *A61C 13/0004* (2013.01); *A61C 13/0013* (2013.01); *A61C 13/0018* (2013.01); *A61C 13/0019* (2013.01); *B29C 67/0088* (2013.01); *G05B 19/4097* (2013.01); *B33Y 10/00* (2014.12); *B33Y 50/02* (2014.12); *B33Y 80/00* (2014.12)

(56) References Cited

U.S. PATENT DOCUMENTS

| | | | |
|---|---|---|---|
| 2013/0171580 A1* | 7/2013 | Van Lierde | A61B 6/14 433/29 |
| 2013/0209961 A1 | 8/2013 | Rubbert et al. | |
| 2014/0147815 A1* | 5/2014 | Sicurelli | A61C 13/30 433/220 |

FOREIGN PATENT DOCUMENTS

| | | | |
|---|---|---|---|
| IT | WO 2014115090 A1 * | 7/2014 | A61C 5/04 |
| WO | WO 2014/115090 A1 | 7/2014 | |

OTHER PUBLICATIONS

Gutmann et al., "Root Canal Obturation: An Update", Academy of General Dentistry, not dated, pp. 1-11.

* cited by examiner

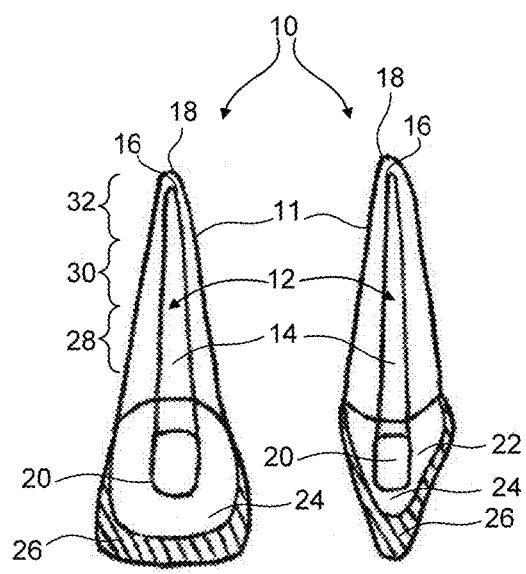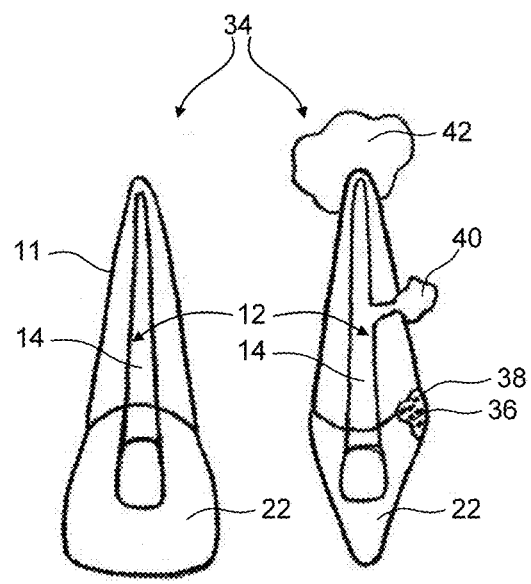
FIG. 1A   FIG. 1B   FIG. 2A   FIG. 2B

| Test | Tooth #8 | Tooth #9 | Tooth #10 |
|---|---|---|---|
| Percussion | Normal | +++ | Normal |
| Palpation | Normal | ++ | Normal |
| Cold | Normal | - | Normal |
| Hot | Normal | +++ lingering | Normal |
| Electric Pulp Test | Normal | No response | Normal |
| Biting | Normal | +++ | Normal |
| Mobility | Normal | + | Normal |
| Discoloration of Crown | Normal | Discolored, gray | Normal |
| Periodontal Findings | Normal | Normal | Normal |

FIG. 5

CUSTOMIZED ROOT CANAL OBTURATION CORES AND METHODS OF MAKING CUSTOMIZED ROOT CANAL OBTURATION CORES

BACKGROUND

Field

Embodiments of the present inventions are generally related to root canal obturation and more specifically to customized root canal obturation cores and methods of and systems for making customized root canal obturation cores.

Background

A tooth includes a root canal that encases a pulp. Bacteria introduced into the pulp can cause inflammation or infection. Once the pulp becomes inflamed or infected, the pulp can be removed to restore the area to health. To prevent bacteria from entering the root canal after removing the pulp, the canal is obturated using a filler material. The filler material typically includes, for example, gutta percha placed incrementally with lateral compaction of individual gutta percha cones, gutta percha placed incrementally with warm vertical compaction, a single gutta percha cone, gutta percha on a carrier of a similar or different core material, a polymeric hydrogel attached to a central nylon core, or a sealer-only material applied to the full length of the canal.

An obturation with voids in the root canal and leakage between the filler material and the root canal increases the risk of re-infection and reduces the chance of long-term success of the root canal procedure. There are typically two kinds of leakage: (1) coronal leakage and (2) lateral canal or apical leakage. Coronal leakage refers to when microorganisms from the oral cavity enter the root canal system via seepage in the restorative seal covering the filler material. Lateral canal or apical leakage occurs when the lateral and apical root segments are infiltrated by peptides and other molecules from the surrounding tissues that support microbial growth in the obturated root canal system. Microbial infiltration of the root canal system obturated with gutta percha can occur in as little as three weeks. Filler materials used today, except for paste-only obturation techniques, typically consist of using a solid core material placed with a paste or sealer component. These techniques can generate significant voids in the root canal, which can lead to leakage, infection, and eventual re-treatment or tooth loss. And it is difficult to entirely fill ribbon-shaped and widely oval-shaped canals. According, there is a need for an obturation system that substantially fills the entire root canal without voids for variously shaped root canals.

BRIEF SUMMARY

In some embodiments, a core for obturating a root canal includes a body that has a pre-formed contour that closely matches a contour of the prepared and disinfected root canal. When the core is inserted in the root canal, there are essentially no voids in the root canal.

In some embodiments, a method of making a customized root canal obturation core includes generating a three-dimensional image of a root canal. The method also includes manufacturing the customized root canal obturation core based on the three-dimensional image of the root canal. The customized root canal obturation core has a contour that closely matches a contour of the root canal such that when the core is inserted in the root canal there are essentially no voids in the root canal.

In some embodiments, a method of treating pulpal damage includes generating a three-dimensional image of a root canal. The method also includes manufacturing the customized root canal obturation core based on the three-dimensional image of the root canal. The customized root canal obturation core has a contour that closely matches a contour of the root canal. The method further includes inserting the customized root canal obturation core into the root canal such that there are essentially no voids in the root canal.

In some embodiments, a system for generating a customized root obturation core includes a computational device comprising a processor configured to extract three-dimensional data from a three-dimensional image of a root canal. The system also includes a computer controlled system configured to manufacture the customized root canal obturation core using the extracted three-dimensional data.

BRIEF DESCRIPTION OF THE DRAWINGS

Embodiments will now be described, by way of example only, with reference to the accompanying schematic drawings in which corresponding reference symbols indicate corresponding parts, and in which:

FIGS. 1A and 1B illustrate (1) a coronal view of a human anterior tooth and (2) a sagittal view of the human anterior tooth of FIG. 1A, respectively.

FIGS. 2A and 2B illustrate (1) a coronal view of an abscessed human anterior tooth and (2) a sagittal view of the human anterior tooth of FIG. 2A, respectively.

FIG. 5 illustrates an exemplary tooth testing matrix.

Figure 3:
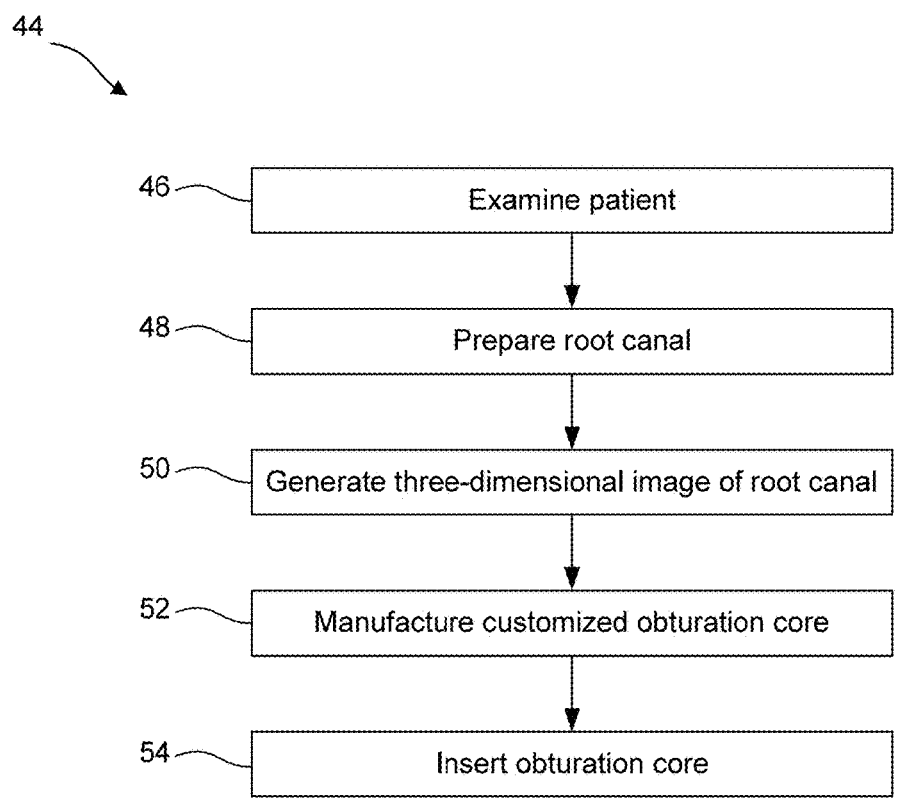
FIG. 3 illustrates a block diagram of a method of treating pulpal damage according to an embodiment.

Features and advantages of the embodiments of the present invention will become more apparent from the detailed description set forth below when taken in conjunction with the drawings.

DETAILED DESCRIPTION

While the invention is described herein with reference to illustrative embodiments for particular applications, it should be understood that the invention is not limited thereto. Those skilled in the art with access to the teachings provided herein will recognize additional modifications, applications, and embodiments within the scope thereof and additional fields in which the invention would be of significant utility.

FIGS. 1A and 1B illustrate a coronal view of a human anterior tooth 10 and a sagittal view of tooth 10, respectively. Tooth 10 includes a root 11 that defines a root canal 12 that contains a pulp 14. Pulp 14 is soft tissue that includes blood vessels, connective tissue, and nerves. Pulp 14 can extend from a physiologic apex 16, which is usually located about 0.5 mm from a radiographic apex 18, to a pulp horn 20 at a crown 22 of tooth 10. Crown 22 is typically composed of dentin 24 and a layer of enamel 26 that covers dentin 24. Root canal 12 can include a coronal portion 28 (the portion nearest crown 22), a middle portion 30, and an apical portion 32 (the portion nearest physiological apex 16), extending from crown 22 to physiological apex 16.

FIGS. 2A and 2B illustrate (1) a coronal view of an abscessed human anterior tooth 34 and (2) a sagittal view of tooth 34, respectively. Sometimes bacteria 36 is introduced into pulp 14 in root canal 12. For example, bacteria 36 can be introduced by caries 38 in tooth 34, periodontal disease, or a fracture. Sometimes bacteria 36 causes inflammation or infection in the surrounding bone, for example, in close approximation to a lateral or accessory canal 40 or to a physiologic terminus 42 of canal 12. Inflammation or infection can cause pain and swelling. Damage to pulp 14 may also occur even if the tooth has no visible deterioration, for example, caries 38. Once pulp 14 becomes inflamed or infected, a root canal or extraction can be necessary to remove the affected tissue and to restore the area back to health.

FIG. 3 illustrates a block diagram of a method 44 for treating pulpal damage according to an embodiment. Method 44 includes a patient examination step 46, a root canal preparation step 48, a three-dimensional image generation step 50, an obturation core manufacturing step 52, and an obturation core insertion step 54.

Figure 4:
FIG. 4 is an exemplary periapical radiograph of a maxillary left central incisor.

In some embodiments, at patient examination step 46, a dentist, for example, a general dentist or an endodontist, conducts an examination of the patient. During the examination, the dentist can interview the patient and review the patient medical and dental history. In some embodiments at step 46, the dentist exposes a planar—two-dimensional—radiographic image of the tooth or teeth of interest. FIG. 4 is an exemplary periapical radiographic image of a maxillary left central incisor could be obtained during the exam. The dentist can evaluate the planar radiographic image and then perform a physical examination.

In some embodiments at step 46, the physical examination includes recording responses to various tests including, for example, percussion, palpation, bite stick, thermal, transillumination, and electrical pulp tests. During the physical examination, the dentist can test for signs of pulpal damage, for example, pain on percussion, sensitivity to hot or cold, color changes, soreness, or swelling in the surrounding tissues. These results can be recorded as objective findings in a written matrix such as the one illustrated in FIG. 5. As shown in FIG. 5, the results recorded in the matrix indicate that tooth #9, the maxillary left central incisor, may be infected.

Figure 6:
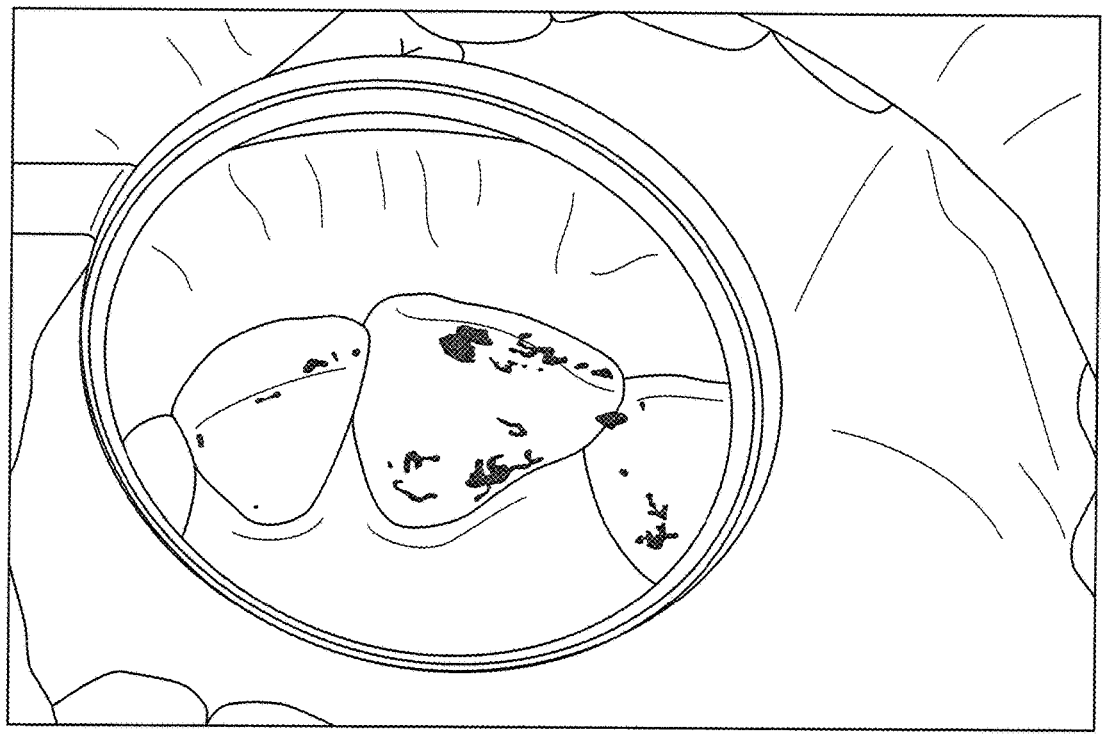
FIG. 6 is a photograph of a central incisor to document the visible light findings and occlusion.

In some embodiments, patient examination step 46 also includes an examination of the tooth or teeth of interest for fracture, for example, by using an explorer, special lighting, and/or using enhanced magnification. In some embodiments, patient examination step 46 also includes an examination of the tooth or teeth of interest for hyper-occlusion. FIG. 6 shows a pre-treatment photographic image that may be exposed to document the examination findings, for example, hyper-occlusion.

Figures 7A, 7B, 7C:
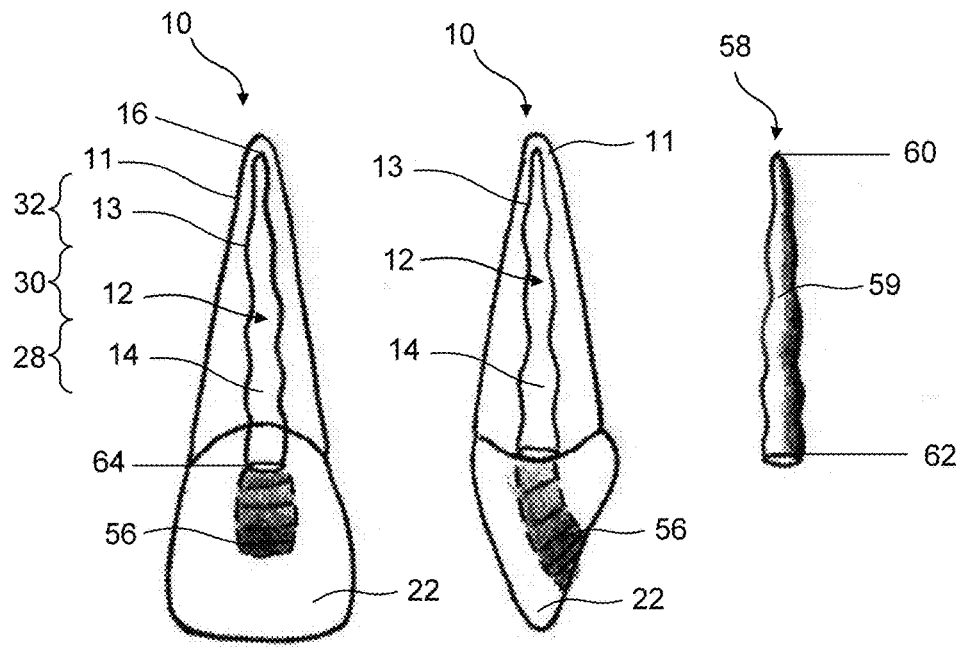
FIGS. 7A, 7B, and 7C illustrate (1) a coronal view of a human anterior tooth after irrigation and cleaning and after minimal or no instrumentation; (2) a sagittal view of the human anterior tooth of FIG. 7A; and (3) a customized obturation core according to an embodiment, respectively.
Figures 8A, 8B, 8C:
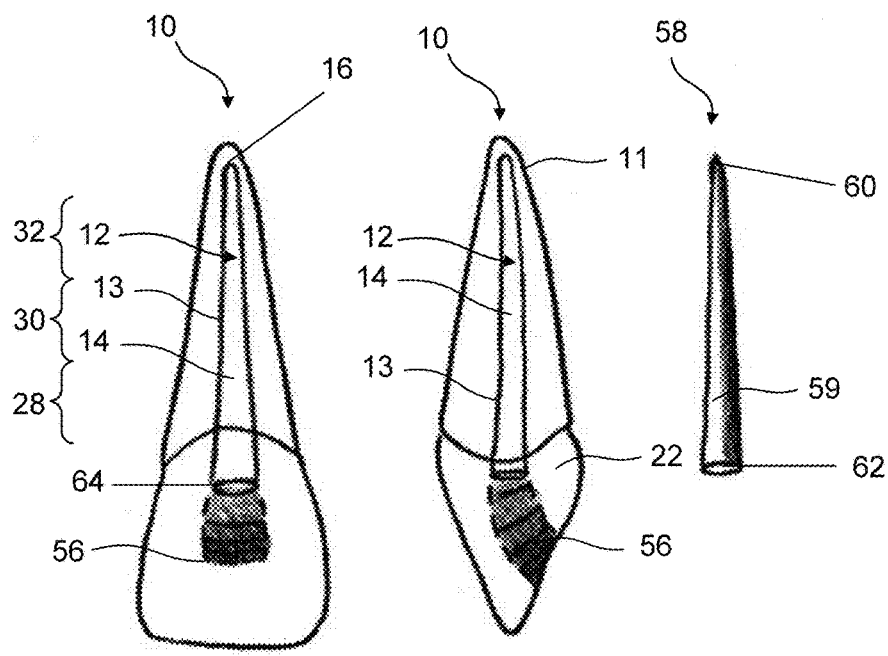
FIGS. 8A, 8B, and 8C illustrate (1) a coronal view of a human anterior tooth after irrigation and cleaning and after instrumentation; (2) a sagittal view of the human anterior tooth of FIG. 8A; and (3) a customized obturation core according to an embodiment, respectively.

Method 44 can also include a root canal preparation step 48. At step 48, the dentist can prepare root canal 12 of tooth 10. In some embodiments, root canal preparation step 48 includes a routine non-surgical procedure for removing pulp 14 from canal 12, for example, through an access opening 56 (referring to FIGS. 7A, 7B, 8A, and 8B) on an exposed surface of tooth 10 in some embodiments. In some embodiments at step 48, after removing pulp 14, root canal 12 is irrigated and disinfected, for example, by providing an irrigant to remove substantially all traces of tissue, debris, and bacteria in root canal 12. For example, canal 12 can be irrigated using a needle that delivers the irrigant. In some embodiments at step 48, as shown in FIGS. 7A and 7B, after irrigating and disinfecting, walls 13 (which form the contour of canal 12) of canal 12 are either uninstrumented or lightly instrumented through access opening 56 using for example, a sonic, multisonic or ultrasonic agitator, a laser technique, or any combination thereof. In some embodiments at step 48, as shown in FIGS. 8A and 8B, after irrigating and disinfecting, the walls of canal 12 are moderately or heavily instrumented so that walls 13 of canal 12 form a desired shape. For example, as shown in FIGS. 8A and 8B, walls 13 of canal 12 form a conical shape. In some embodiments, the desired shape of walls 13 of canal 12 is a non-conical shape.

In some embodiments, root canal preparation step 48 includes a revision procedure. That is, root canal 12 is retreated or revised because of continued infection after initial treatment, which can sometimes occur years later. Revision procedures can be necessary when there was an incomplete prior root canal therapy, complicated canal anatomy, or contamination with oral bacteria through a leaking restoration. In some embodiments in which root canal preparation step 48 is a revision procedure, the previously placed root canal filling material is removed from canal 12, and canal 12 is irrigated and disinfected. In some embodiments in which root canal preparation step 48 is a revision procedure, root canal preparation step 48 is performed using an operating microscope along with digital radiography.

In some embodiments, root canal preparation step 48 is surgical procedure that includes, for example, surgically removing infected root 11 or apex 16 and the surrounding tissue. This procedure is known as apical micro-surgery or an apicoectomy. A surgical operating microscope with special coaxial lighting can be used to enhance visualization during such procedures.

Method 44 can also include a three-dimensional image generation step 50. At step 50, a three-dimensional image that includes, at least in part, canal 12 is generated. In some embodiments, the three-dimensional image is a high-resolution three-dimensional image, for example, an image having a resolution in the range of about 75-90 μm voxel size. In some embodiments, the three-dimensional image has a resolution outside of the range of about 75-90 μm voxel size.

In some embodiments at image generation step 50, one or more three-dimensional images are generated.

Figure 9A:
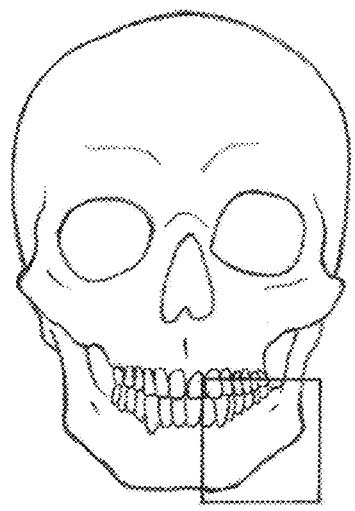
FIGS. 9A, 9B, and 9C illustrate a schematic view of a human skull with, from the left, a limited field of view, a medium field of view, and a large field of view, respectively, according to an embodiment.
Figure 9B:
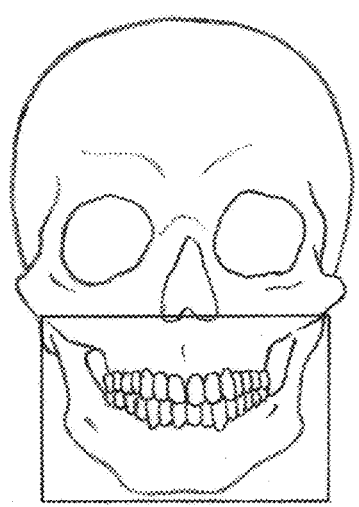
Figure 9C:
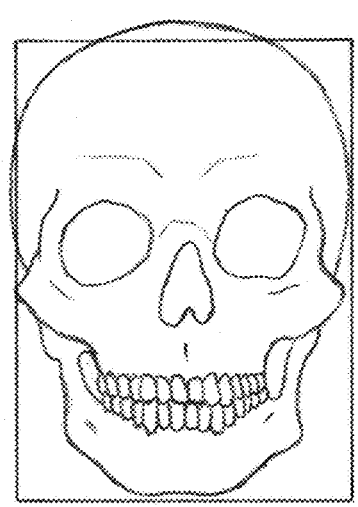
Figure 10A:
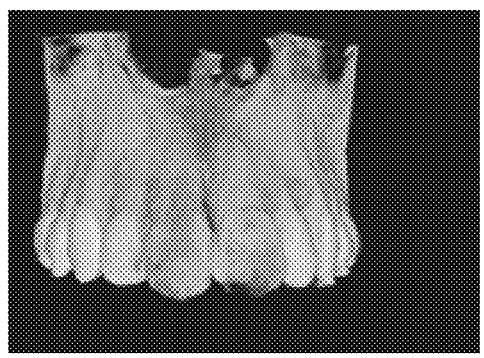
FIGS. 10A-10D illustrate exemplary generated three-dimensional images.
Figure 10B:
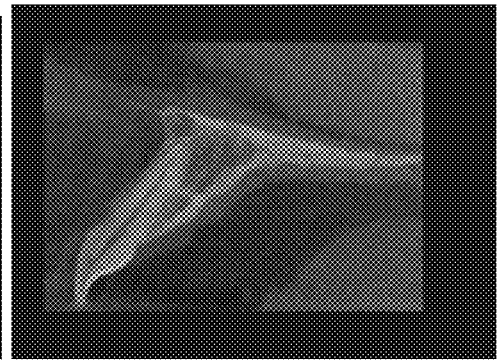
Figure 10C:
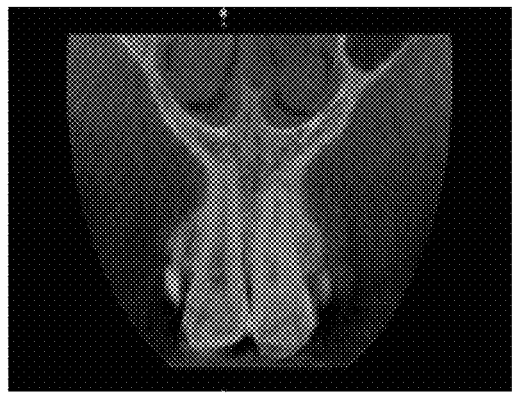
Figure 10D:
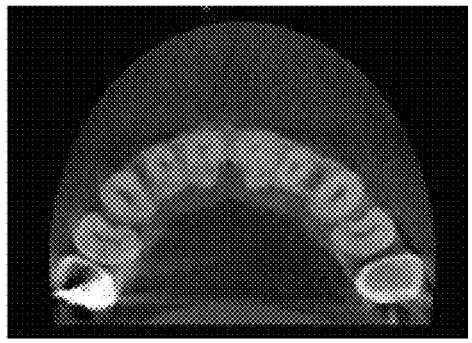

In some embodiments, the three-dimensional image is a tomographic image. In some embodiments, the three-dimensional image is generated by computed tomography (CT), for example, using X-ray CT such as a cone-beam CT (CBCT); magnetic resonance imaging (MRI); ultrasound, radiography, optical imaging, or any other suitable three-dimensional imaging technology. The three dimensional image may have various fields of view (FOV). For example, as shown in FIGS. 9A-9C, the generated three-dimensional image may have a limited FOV as illustrated by the box in FIG. 9A, a medium FOV as illustrated by the box in FIG. 9B, or a large FOV as illustrated by the box in FIG. 9C. FIGS. 10A-10D illustrates exemplary generated three-dimensional images showing a view of the reconstructed surface in FIG. 10A, a reconstructed sagittal view in FIG. 10B, a reconstructed coronal view in FIG. 10C, and an axial view in FIG. 10D according to an embodiment. The generated three-dimensional image can show a single tooth, a quadrant of teeth, a sextant of teeth, or the entire dentition and surrounding structures in three dimensions in some embodiments.

In some embodiments, the three-dimensional image is generated intra-operatively and post-operatively—concurrently with or after canal preparation step 48.

In some embodiments, image generation step 50 is performed at a dentist's office. In some embodiments, step 50 is performed at facility outside of the dentist's office.

Method 44 can also include an obturation core manufacturing step 52. At step 52, a customized obturation core 58 is made. FIGS. 7C and 8C illustrate exemplary obturation cores 58. In some embodiments at step 52, a body 59 of obturation core 58 is shaped so its preformed contour (i.e., its contour before being inserted into canal 12) closely matches the contour of walls 13 of root canal 12. In some embodiments, the contour of body 59 of core 58 closely matches the contour of walls 13 of root canal 12 such that substantially the entire canal 12 is filled with only core 58 when inserted therein—there are essentially no voids in canal 12 at coronal portion 28, middle portion 30, and apical portion 32. As used in this application, essentially no voids in the canal means that the gap between any portion of core 58 and walls 13 of root canal 12 is smaller than at least about 2.0 micrometers—the average size of bacterium. In some embodiments, the gap between any portion of core 58 and walls 13 of root canal 12 is smaller than about 0.5 micrometers. In some embodiments, the contour of body 59 of core 58 closely matches the contour of walls 13 of root canal 12 such that substantially the entire canal 12 is filled with core 58 and a sealant when inserted therein—there are essentially no voids in canal 12 at coronal portion 28, middle portion 30, and apical portion 32.

In some embodiments, the contour of the body of core 58 is substantially parallel to the contour of root canal 12. In some embodiments, core 58 is made to have an initial volume of about 90 to 110 percent of the volume of root canal 12. In some embodiments, core 58 is about have an initial volume of about 95 to 105 percent of the volume of root canal 12. For example, as shown in FIG. 7C, body 59 of core 58 has a wavy contour that closely matches the wavy contour of walls 13 of canal 12 in FIGS. 7A and 7B. As shown in FIG. 8C, body 59 of core 58 has a substantially conical contour that closely matches the conical contour of walls 13 of canal 12 in FIGS. 8A and 8B. In some embodiments, core 58 has a preformed shape that includes an intermediate portion that has a smaller diameter than proximal and distal portions of core 58, for example, an hourglass shape.

Figure 16C:
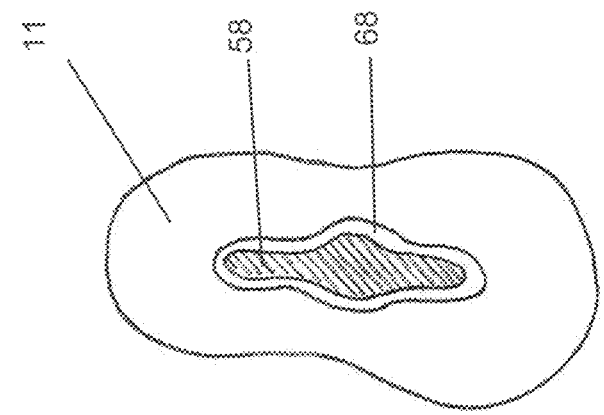
FIGS. 16A, 16B, and 16C illustrate cross-sectional views of a root and root canal after instrumentation and disinfection with no core and sealant, with a conventional core and sealant, and a customized obturation core and sealant according to an embodiment, respectively.
Figure 16B:
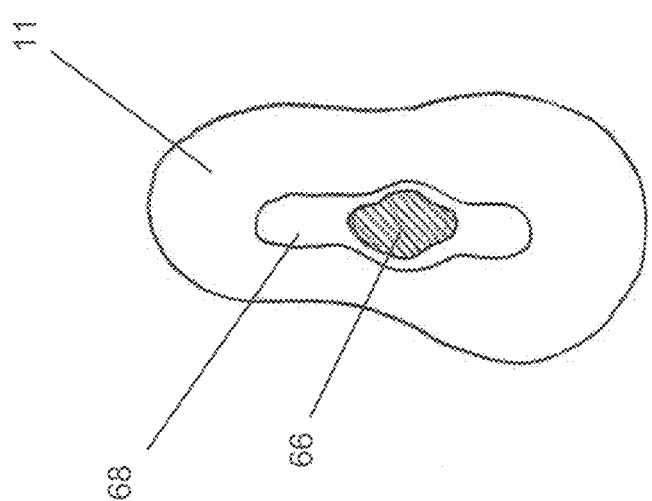
Figure 16A:
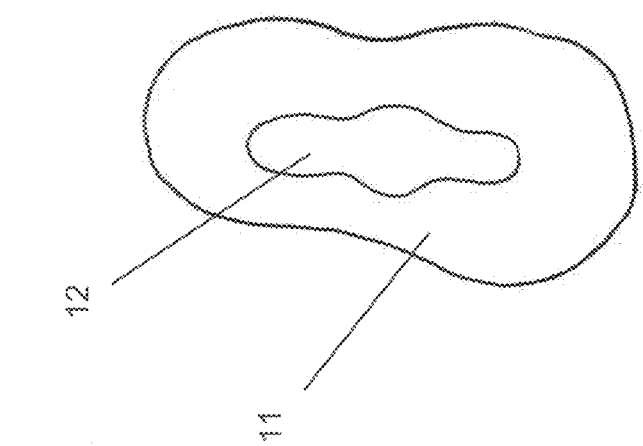

In some embodiments in which core 58 is used with a sealant, core 58 is sized to minimize the volume of sealant used relative to a conventional obturation core that uses a sealant. For example, referencing FIGS. 16A, 16B, and 16C which illustrate cross-sectional views of root 11 and root canal 12 (1) with no core and sealant, (2) with a conventional core 66 and sealant 68, and (3) with customized obturation core 58 and sealant 68 according to an embodiment, respectively, the volume of sealant 68 required to entirely fill canal 12 with core 58 such that there are essentially no voids in canal 12 is less than the volume of sealant 68 required to fill canal 12 with conventional core 66. Reducing the volume of sealant 68 required to fill canal 12 reduces the risk that sealant 68 will deteriorate and, thus, allow bacteria to infiltrate canal 12.

In some embodiments, a postoperative radiograph of a tooth using customized core 58 will have a better radiographic appearance than a tooth using a conventional core 66. That is, because of the close-fit of core 58, the filled root canal 12 will have a better appearance that indicates the highly accurate fitting of core 28 to canal walls 13.

In some embodiments, as shown in FIGS. 7A, 7C, 8A, and 8C, core 58 has a length such that, when core 58 is inserted in canal 12, an apical end 60 of core 58 is positioned at physiologic apex 16, and a coronal end 62 of core 58 is positioned at the orifice 64 of canal 12. In other embodiments, core 58 has a length such that, when core 58 is inserted in canal 12, apical end 60 is positioned at physiologic apex 16, and coronal end 62 is positioned proximate to access opening 56.

In some embodiments, obturation core 58 is made of a sterile material. In some embodiments, obturation core 58 is an inert material. In some embodiments, obturation core 58 is a biocompatible material. In some embodiments, obturation core 58 is a sterile, inert, and biocompatible material. In some embodiments, obturation core 58 is made of a sterile, inert, and/or biocompatible material. In some embodiments, core 58 is made of a material that is antimicrobial to reduce the risk that bacteria will grow in canal 12. In some embodiments, core 58 is made of a material that is substantially impervious to bacterial infiltration. In some embodiments, core 58 is made of a material that can be safely applied to avoid overextension into vital anatomic structures. In some embodiments, core 58 is made of a material that is radiopaque. In some embodiments, the obturation core 58 comprises gutta percha, nylon, plastic, or any other material of a desired level of cleanliness, biocompatibility, inertness, and inherent antimicrobial activity.

In some embodiments, obturation core 58 comprises an expansive biocompatible material. For example, obturation core 58 can be made from a material that expands when exposed to a catalyst, for example, moisture or a sealant for cementing core 58 to tooth 10. In such embodiments, obturation core 58 is manufactured such that upon expansion in situ obturation core 58 achieves about 100 percent or more than about 100 percent of the volume of root canal 12 such that with sealer there are essentially no voids in canal 12. In some embodiments, the expansion ratio of core 58 is constant along the length of core 58. Notably, although the expansion ratio may be constant along the length of core 58, the absolute diametric expansion may vary depending upon the initial preformed diameter of core 58. For example, if core 58 has a 105 percent diametric expansion ratio and the initial shape of core 58 has a 2 mm diameter bottom and a 10 mm diameter top, the bottom diameter will expand 0.1 mm, and the top diameter will expand 0.5 mm. In other embodiments, different longitudinal segments of core 58 can have different expansion ratios. Thus, for example, the distal segment can be configured to have a higher expansion ratio than the proximal segment. Likewise, the proximal segment can be configured to have a higher expansion ratio than the distal segment. Due to the variable dimensions of a patient's root canal, it is understood that the diameter and shape of the obturation core would vary along its length to match imaged shape of the patient's root canal. It is also understood that an expansive material having different diameters along its length will expand differently.

In some embodiments, obturation core 58 comprises a non-expansive material.

In some embodiments, obturation core 58 comprises a material that does not diametrically contract over an extended period of time, for example, at least 10 years, at least 20 years, at least 30 years, or a lifetime.

In some embodiments at step 52, obturation core 58 is manufactured by a system comprising a computational device comprising a processor configured to generate a three-dimensional CAD model of either canal 12 or body 59 of core 58, and a computer controlled manufacturing system. The computational device can be, for example, a computer, a PDA, a tablet, or any other suitable computational device comprising a processor.

The computer controlled manufacturing system can be, for example, a computer numerically controlled machine, an additive manufacturing machine, or any other suitable manufacturing machine. In some embodiments in which the computer controlled manufacturing system is a computer numerically controlled machine, the computer numerically controlled machine can include a lathe, a milling device, or any other subtractive machine. In some embodiments in which the computer controlled manufacturing system is an additive manufacturing machine, the additive manufacturing machine can be a stereolithographic machine, an inkjet printer machine (i.e., a 3D printer), a selective laser sintering machine, a fused deposition modeling machine, or any other suitable additive machine.

In some embodiments, the computer controlled manufacturing system manufactures core 58 using the three dimensional image obtained at step 50. For example, the three dimensional image generated at step 50 can be uploaded to the computational device using computer imaging software and stored in memory on the computational device. The computational device can generate a three-dimensional CAD model of canal 12 or of body 59 of core 58 by using the uploaded three-dimensional image. In some embodiments, the three-dimensional CAD model is made by decomposing root canal 12 into cross-sectional layer representations. In some embodiments, the computational device uses the three-dimensional CAD model to generate instructions, for example, numerical files, that drive the computer controlled system to manufacture body 59 of core 58, and then the computational device transmits the instructions to the computer controlled manufacturing system. In some embodiments, the computational device is separate from the computer controlled system. In some embodiments, the computational device is integral with the computer controlled system.

Figure 11:
FIGS. 11-15 illustrate screen shots of exemplary imaging software used to segment a three-dimensional image and to render a volumetric analysis of the root canal.
Figure 12:
Figure 13:
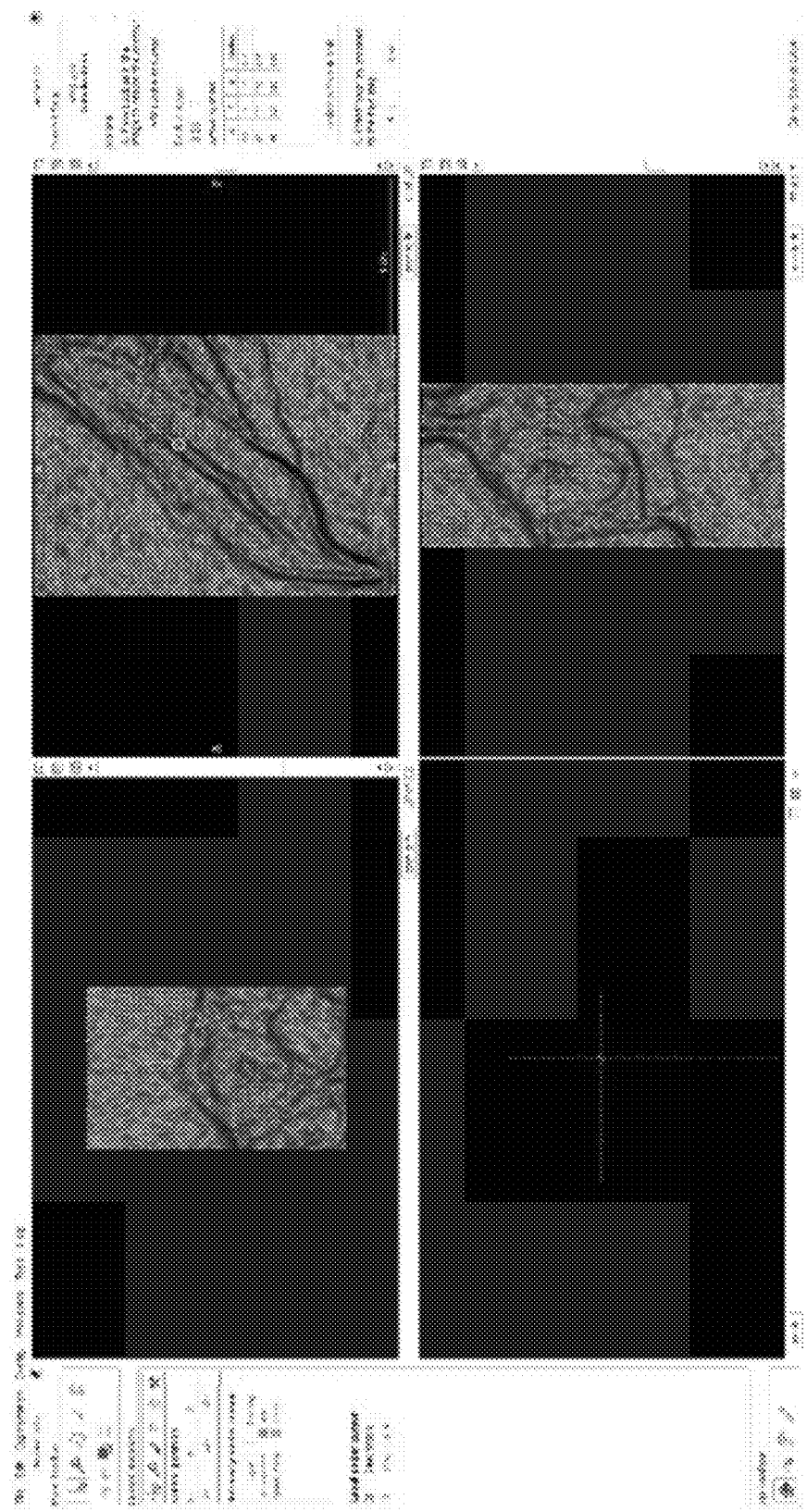

FIGS. 11-15 illustrate screen shots of exemplary imaging software running on the computational device for generating a three-dimensional CAD model of canal 12 or body 59 of core 58. Particularly, FIG. 11 illustrates a step of uploading the generated three-dimensional image to the computational device. Using the software, a user can identify, for example, by outlining, a region of interest of tooth 10, for example, canal 12, on a graphical user interface on a display of the computational device as illustrated in FIG. 12. Then in some embodiments, the software generates a three-dimensional CAD model of canal 12. For example, FIG. 13 illustrates an exemplary screen shot for adjusting the automatic segmentation tool for performing the segmentation iterations with appropriate landmarks applied to generate a three-dimensional CAD model of canal 12 (or core 58). In some embodiments, the software simply and quickly automatically segments root canal 12 and highlights the lateral or accessory canals.

Figure 14:
Figure 15:
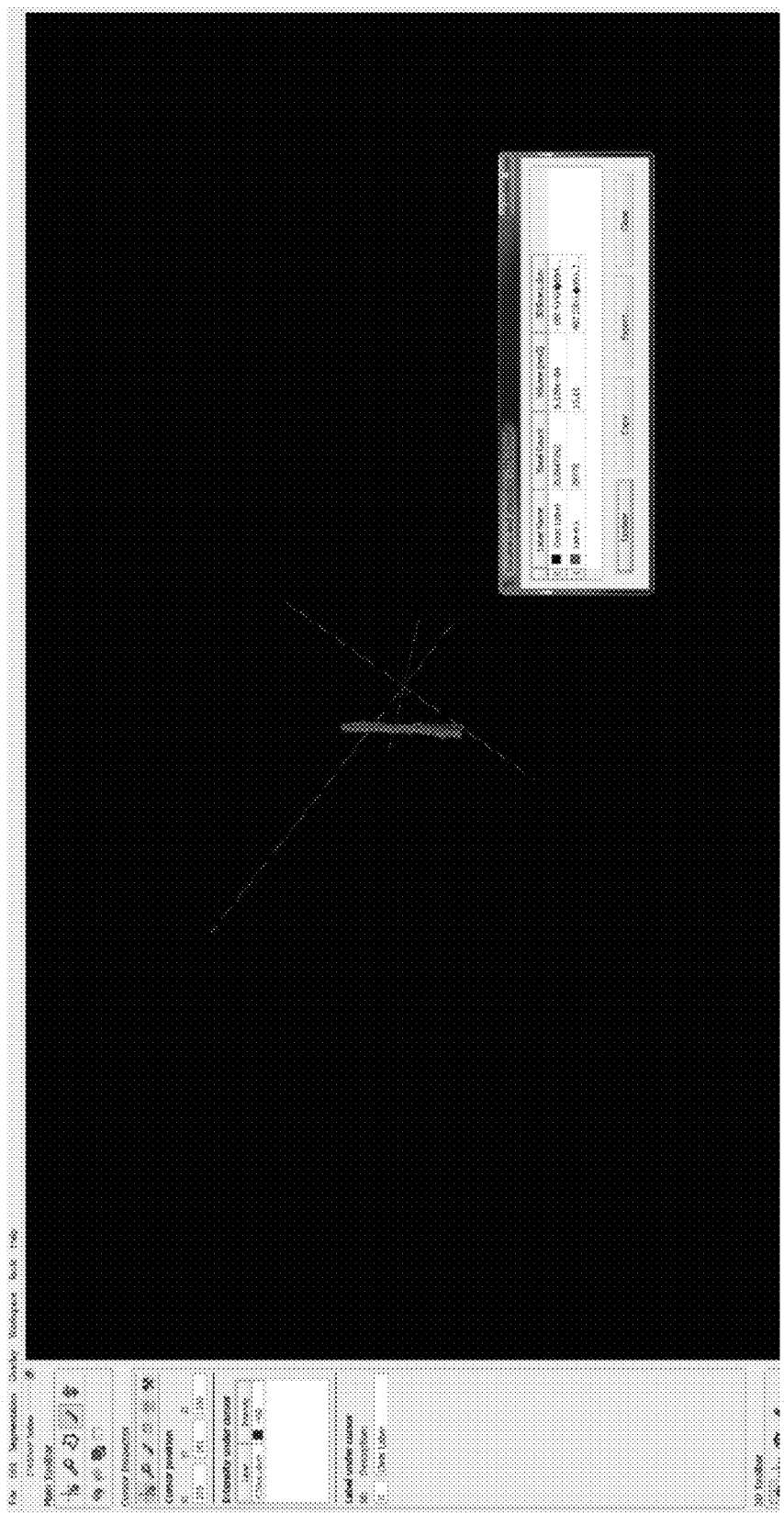

In some embodiments, this CAD model generation substep includes measuring the length and width of canal 12. In some embodiments, the length of canal 12 is measured from physiological apex 16 to access opening 56. In other embodiments, the length of canal 12 is measured from physiological apex 16 to orifice 64 of the canal 12. FIG. 14 illustrates an exemplary screen shot of the graphical user interface for measuring the length and width of canal 12. In some embodiments, the width and length of canal 12 is determined in a slice-by-slice format, for example, by using voxel count and volume. The software then generates a three-dimensional CAD model of canal 12 or body 59 of core 58. FIG. 15 illustrates an exemplary three-dimensional CAD model of body 59 of core 58. From the three-dimensional CAD model, the computational device can generate the file(s) for driving the computer controlled manufacturing system, for example, number files, to make core 58.

In some embodiments, the software superimposes core 58 within canal 12 to allow a user to assess how core 58 fills canal 12 and to verify that core 58 fills the entire canal 12 without forming voids.

In some embodiments core generation step 52 occurs at the dentist's office. In some embodiments, core generation step 52 occurs at a facility off-site from dentist's office, and core 58 is shipped to the dentist.

After generating core 58 at step 52, a dentist inserts core 58 within canal 12 at step 54 of method 44. In some embodiments, core 58 is inserted in canal 12 without using a sealant. In some embodiments, core 58 is inserted in canal 12 with a sealant to cement core 58 to tooth 10. In some embodiments in which a sealant is used, canal 12 is coated with sealant before inserting core 58 into canal 12, core 58 is coated with sealant, or both. In some embodiments, when core 58 is inserted into canal 12 with or without using sealant, canal 12 is fully sealed without voids. In some embodiments, a sealant is used to cement core 58 to canal 12. In some embodiments, when inserted, core 58 renders canal 12 substantially impervious to bacterial infiltration or entombs any remaining bacteria in canal 12.

In some embodiments, step 52 also includes placing a permanent restoration in access opening 56 to seal core 58 within canal 12.

In some embodiments, core 58 can be inserted into canal 12 with minimal, for example, because the preformed contour of body 59 of core 58 closely matches the contour of canal 12. Accordingly, the risk of tooth fracture can be minimized.

In some embodiments, one or more of steps 46, 48, 50, and 52 are omitted form method 44. For example, steps 46 and 52 may be omitted.

While various embodiments of the present invention have been described above, it should be understood that they have been presented by way of example, and not limitation. It will be apparent to persons skilled in the relevant art that various changes in form and detail can be made therein without departing from the spirit and scope of the invention.

The present invention has been described above with the aid of functional building blocks and method steps illustrating the performance of specified functions and relationships thereof. The boundaries of these functional building blocks and method steps have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like or any combination thereof. Thus, the breadth and scope of the present invention should not be limited by any of the above-described exemplary embodiments, but should be defined only in accordance with the following claims and their equivalents.

What is claimed:

1. A core for obturating a root canal having a coronal portion, a middle portion, and an apical portion, the core comprising:
   a pre-formed contoured portion that closely matches a contour of the apical portion of the root canal such that when the pre-formed contoured portion is inserted in the apical portion of the root canal with or without a sealant any voids between the pre-formed contoured portion and a wall of the apical portion of the root canal are smaller than about 2.0 micrometers, thereby creating a seal substantially impervious to bacteria.

2. The core of claim 1, wherein the pre-formed contoured portion comprises a material that is biocompatiable and substantially impervious to bacterial infiltration.

3. The core of claim 1, wherein the pre-formed contoured portion is generated by a computerized manufacturing system that uses a three-dimensional image of the root canal.

4. A method of making a customized root canal obturation core, the method comprising:
   generating a three-dimensional image of a hollow root canal from which inflamed or infected tissue has been removed, the root canal having a coronal portion, a middle portion, and an apical portion; and
   manufacturing the root canal obturation core based on the three-dimensional image of the root canal, the customized root canal obturation core comprising a pre-formed contoured portion that closely matches a contour of the apical portion of the root canal such that when the pre-formed contoured portion is inserted in the apical portion of the root canal with or without sealant any voids between the pre-formed contoured portion and a wall of the apical portion of the root canal are smaller than about 2.0 micrometers, thereby creating a seal substantially impervious to bacteria.

5. The method of claim 4, wherein the three-dimensional image is a tomographic image.

6. The method of claim 4, wherein generating the three-dimensional image comprises using computed tomography (CT), magnetic resonance imaging (MRI), ultrasound imaging, or optical imaging.

7. The method of claim 4, wherein manufacturing the root canal obturation core based on the three-dimensional image of the root canal comprises:
   generating a three-dimensional model of the root canal or of the root canal obturation core from the three-dimensional image; and
   using a computer controlled manufacturing system to manufacture the root canal obturation core based on the three-dimensional model of the root canal or of the root canal obturation core.

8. The method of claim 7, wherein the computer controlled manufacturing system comprises a computer numerically controlled lathe or a milling machine.

9. The method of claim 7, wherein the computer controlled manufacturing system comprises an additive manufacturing machine.

10. The method of claim 9, wherein the additive manufacturing machine comprises a stereolithographic machine, an inkjet printer machine, a selective laser sintering machine, or a fused deposition modeling machine.

11. A method of treating pulpal damage, the method comprising:
    removing inflamed or infected tissue from a root of a tooth, thereby creating a hollow root canal having a coronal portion, a middle portion, and an apical portion;
    generating a three-dimensional image of the root canal;
    manufacturing the customized root canal obturation core based on the three-dimensional image of the root canal, the customized root canal obturation core comprising a pre-formed contoured portion that closely matches a contour of the apical portion of the root canal; and
    inserting the customized root canal obturation core into the root canal with our without sealant such that the pre-formed contoured portion is positioned at the apical portion of the root canal and that any voids between the pre-formed contoured portion and a wall of the apical portion of the root canal are smaller than about 2.0 micrometers, thereby creating a seal substantially impervious to bacteria.

12. The method of claim 11, further comprising removing a pulp from the root canal.

13. The method of claim 11, wherein the three-dimensional image is a tomographic image.

14. The method of claim 11, wherein generating the three-dimensional image comprises using computed tomography (CT), magnetic resonance imaging (MRI), ultrasound imaging, or optical imaging.

15. The method of claim 11, wherein manufacturing the customized root canal obturation core based on the three-dimensional image of the root canal comprises:
    generating a three-dimensional model of the root canal or of the root canal obturation core from the three-dimensional image; and
    using a computer controlled manufacturing system to manufacture the customized root canal obturation core based on the generated three-dimensional model of the root canal or of the root canal obturation core.

16. The method of claim 15, wherein the computer controlled manufacturing system comprises a computer numerically controlled machine.

17. The method of claim 16, wherein computer numerically controlled machine comprises a lathe or a milling machine.

18. The method of claim 15, wherein the computer controlled manufacturing system comprises an additive manufacturing machine.

19. The method of claim 18, wherein the additive manufacturing machine comprises a stereolithographic machine, an inkjet printer machine, a selective laser sintering machine, or a fused deposition modeling machine.

20. A system for generating a customized core for obturating a root canal having a coronal portion, a middle portion, and an apical portion, the system comprising:
    a computational device comprising a processor configured to generate a three-dimensional model of a root canal or the core from a three-dimensional image of the root canal; and
    a computer controlled manufacturing system configured to manufacture the core using the three-dimensional model, the core comprising a pre-formed contoured portion that closely matches a contour of the apical portion of the root canal such that when the pre-formed contoured portion is inserted in the apical portion of the root canal with or without sealant any voids between the pre-formed contoured portion and a wall of the apical portion of the root canal are smaller than about 2.0 micrometers, thereby creating a seal substantially impervious to bacteria.

21. The system of claim 20, wherein the computer controlled manufacturing system comprises a computer numerically controlled machine.

22. The system of claim 21, wherein computer numerically controlled machine comprises a lathe or a milling machine.

23. The system of claim 20, wherein the computer controlled manufacturing system comprises an additive manufacturing machine.

24. The system of claim 23, wherein the additive manufacturing machine comprises a stereolithographic machine, an inkjet printer machine, a selective laser sintering machine, or a fused deposition modeling machine.

25. The core of claim 1, further comprising:
    a second pre-formed contoured portion that closely matches a contour of the middle portion of the root canal such that when the second pre-formed contoured portion is inserted in the middle portion of the root canal with or without a sealant any voids between the second pre-formed contoured portion and a wall of the middle portion of the root canal are smaller than about 2.0 micrometers, thereby creating a seal substantially impervious to bacteria; and
    a third pre-formed contoured portion that closely matches a contour of the coronal portion of the root canal such that when the third pre-formed contoured portion is inserted in the coronal portion of the root canal with or without a sealant any voids between the third pre-formed contoured portion and a wall of the coronal portion of the root canal are smaller than about 2.0 micrometers, thereby creating a seal substantially impervious to bacteria.

26. The method of claim 4, wherein the customized root canal obturation core further comprises:
    a second pre-formed contoured portion that closely matches a contour of the middle portion of the root canal such that when the second pre-formed contoured portion is inserted in the middle portion of the root canal with or without sealant any voids between the second pre-formed contoured portion and a wall of the middle portion of the root canal are smaller than about 2.0 micrometers, thereby creating a seal substantially impervious to bacteria; and
    a third pre-formed contoured portion that closely matches a contour of the coronal portion of the root canal such that when the third pre-formed contoured portion is inserted in the coronal portion of the root canal with or without sealant any voids between the third pre-formed contoured portion and a wall of the coronal portion of the root canal are smaller than about 2.0 micrometers, thereby creating a seal substantially impervious to bacteria.

27. The method of claim 11, wherein:
    the customized root canal obturation core further comprises:
        a second pre-formed contoured portion that closely matches a contour of the middle portion of the root canal, and
        a third pre-formed contoured portion that closely matches a contour of the coronal portion of the root canal; and
    the inserting the customized root canal obturation core into the root canal comprises:
        positioning second pre-formed contoured portion at the middle portion of the root canal such that any voids between the second pre-formed contoured portion and a wall of the middle portion of the root canal are smaller than about 2.0 micrometers, thereby creating a seal substantially impervious to bacteria, and
        positioning third pre-formed contoured portion at the coronal portion of the root canal such that any voids between the third pre-formed contoured portion and a wall of the coronal portion of the root canal are smaller than about 2.0 micrometers, thereby creating a seal substantially impervious to bacteria.

28. The system of claim 20, wherein the core further comprises a second pre-formed contoured portion that closely matches a contour of the middle portion of the root canal, and a third pre-formed contoured portion that closely matches a contour of the coronal portion of the root canal;
    wherein when the second pre-formed contoured portion is inserted in the middle portion of the root canal with or without sealant any voids between the second pre-formed contoured portion and a wall of the middle portion of the root canal are smaller than about 2.0 micrometers, thereby creating a seal substantially impervious to bacteria; and
    wherein when the third pre-formed contoured portion is inserted in the coronal portion of the root canal with or without sealant any voids between the third pre-formed contoured portion and a wall of the coronal portion of the root canal are smaller than about 2.0 micrometers, thereby creating a seal substantially impervious to bacteria.

* * * * *